Figure 1:
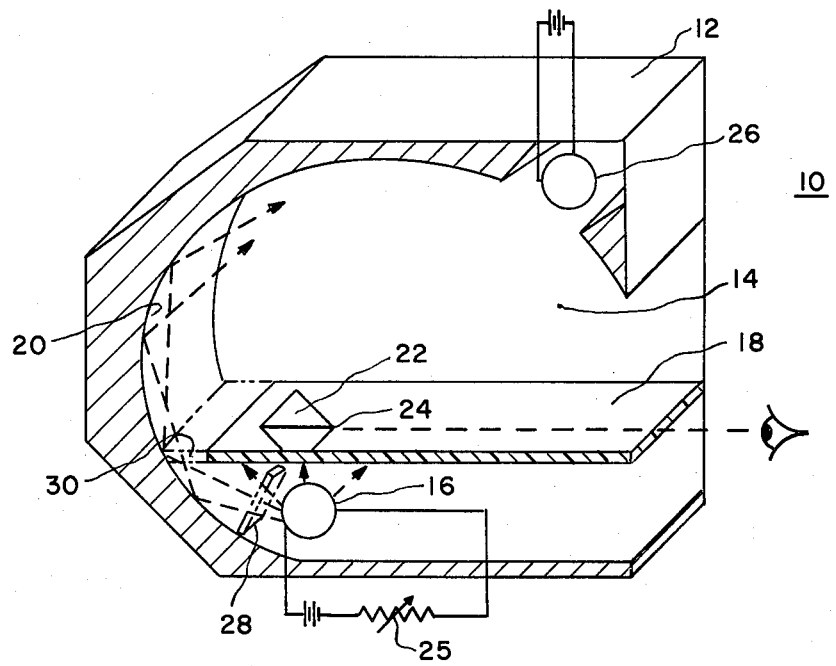

United States Patent [19]
Beesley

[11] 3,944,368
[45] Mar. 16, 1976

[54] APPARATUS FOR COLOR ANALYSIS OF PRECIOUS STONES

[76] Inventor: Casper R. Beesley, 210 Commonwealth Ave., Mount Vernon, N.Y. 10552

[22] Filed: July 11, 1973

[21] Appl. No.: 378,275

[52] U.S. Cl. .................................................. 356/30
[51] Int. Cl.² ........................................... G01N 21/00
[58] Field of Search ................................. 356/30, 72

[56] References Cited
UNITED STATES PATENTS
1,744,485    1/1930    Michel et al. ..................... 356/30

Primary Examiner—Alfred E. Smith
Assistant Examiner—Richard A. Rosenberger

[57] ABSTRACT

A light device for analyzing precious stone body color, comprising a diffused light source in conjunction with indirectly reflected light. Also, method of analyzing precious stones for body color.

12 Claims, 1 Drawing Figure

APPARATUS FOR COLOR ANALYSIS OF PRECIOUS STONES

The present invention relates to an apparatus for analyzing the body color of precious stones and gems and particularly to a light apparatus for such use.

In the appraisal of precious stones, particularly diamonds, one of the important primary factors is the body color of the stone. In order to determine accurately the diamond color, two primarily important factors must be considered, namely, first, the provision of diamonds of predetermined color grades for use as standards with which there can be compared the unknown body color of the examined diamond, and, second, the provision of a constant, uniform light field in which the examined diamond and the standard diamond can be inspected and their respective colors compared.

Diamonds generally have been analyzed for color by inspecting them with illumination from a source above the diamond such that the light is reflected directly on the diamond. Such direct reflection on the diamond has a number of disadvantages, among which is a substantially increased surface reflection from the diamond facets, thereby significantly limiting the color separations. Furthermore, this type of illumination makes it particularly difficult to determine the body color of mounted diamonds by reason of shadows being cast on the stone by the mounting when the diamond is inspected in the "table down" position, which is the characteristic position used for determining body color of diamonds.

The present invention overcomes the disadvantage of these prior art techniques and apparatus by providing a device that supplies a light field of very high uniformity and constancy of intensity and composition and, further, provides the additional benefits of accentuating color differences in diamonds, thereby facilitating the separation of diamond colors into distinct grades on a scale ranging from colorless to yellow.

A still further advantage provided by the present invention minimizes the amount of light reflected from the facet surfaces of the examined diamond, thereby maximizing color distinction, and permits facile and accurate determination of the body colors for mounted, as well as unmounted, diamonds.

The present invention, described generally, comprises a light device that utilizes both diffused light and indirectly reflected light to examine the diamonds. In a preferred embodiment, the light device utilizes light that is transmitted through a light-diffusing plate in conjunction with light reflected indirectly from a curved surface to examine the diamonds.

In a further embodiment, the light device of the present invention comprises a light filter and a light diffusing element in the path between the light source and the curved surface from which the light is reflected. In still another embodiment, the light device comprises an ultraviolet light source that can be employed when the abovementioned light source is turned off, to detect the ultraviolet fluorescence of the diamond.

The present invention is described more particularly in the below preferred embodiments, taken with FIG. 1, which is a sectional isometric view of a light device according to the present invention.

The light device 10 comprises a partial envelope member 12 that partially defines an interior space 14, a primary light source 16 disposed at the space 14 and within the envelope 12, a light-diffusing member 18 disposed in co-operating relation with the light source 16, and a curved light-reflecting surface 20 that is preferably opaque and white and that is situated so as to receive and reflect light originating at the light source 16. The envelope member 12 preferably is light opaque so as to minimize reflectors of ambient light by the diamond that is being examined. The surface 20 can be a part of the envelope wall (as shown) or a separate structure.

In the light device 10, the light-diffusing member 18 is spaced from the light-reflecting surface 20 and a portion of the light radiation from the light source passes through the diffusing member 18, which preferably is translucent and onto the examined diamond 22 which can be disposed on the diffusing member 18 (as shown in FIG. 1, where the diamond is placed in the "table down" position which generally is preferred) or otherwise. Another portion of the light passes from the source 16 through the space between the reflecting surface 20 and the diffusing member 18, to the reflecting surface 20, from which surface the light is reflected upward above the diamond 22. A second diamond (not shown) having known qualities and used as a standard for comparison with the diamond 22 of unknown qualities, is also disposed at the space 14.

In the operation of the light device 10 the light passing through the diffusing member 18 impinges the diamond to illuminate it without surface reflections and the light portion impinging the reflecting surface 20, preferably being white opaque, provides a background against which the respective body colors of the internally illuminated diamonds are compared. The diamond preferably is viewed directly through the girdle 24 at the center section thereof, permitting surface reflection-free examination of the diamond to be made.

It is generally preferred that the light source 16 be a fluorescent or incandescent light, it being further preferred that the light source 16 be connected to a variable power source 25 so as to permit the use of various light intensities.

In another embodiment, the light device 10 further comprises an ultraviolet light source 26 that is used with no light emanating from the light source 16, to detect the ultraviolet fluorescence of the diamond being examined, thus enabling the determination of another quality factor of the unknown diamond.

In still another embodiment, the diffusing member 18 (e.g., a translucent plate of glass, plastic, or other suitable material) extends to the proximity of the light reflecting surface 20 and a light filter 28 is interposed between the diffusing member 18 and the light source 16 in generally the manner shown in FIG. 1, where the extended portion 30 of the diffusing member 18 and the light filter 28 are shown as phantom members.

The present invention has been described in terms of the examined stones' being a diamond; however, the invention can be utilized with a high degree of success in examining stones other than diamonds, which stones, including diamonds, can be mounted or unmounted.

The present invention thus simplifies the color determination of precious stones, provides increased accuracy and repeatability of results, and increases the ability of the observer to accurately separate nuances of the stone's color, particularly in the critical "colorless" and "near colorless" ranges.

I claim:

1. An apparatus for examining a precious stone, comprising:
   a. an envelope structure defining an interior space viewable from without said envelope;
   b. a light source disposed at said interior space;
   c. a white transparent light diffusing means disposed within said interior space;
   d. means for locating said precious stone within said interior space adjacent to said light diffusing means such that said stone is in light receiving relationship with said light diffusing means, and said light diffusing means being disposed between said precious stone and said light source, said stone being viewable from a point outside said interior space; and
   e. means for reflecting light from said light source, and reflecting means being disposed such that said stone is located between said reflecting means and said viewing point, and being arranged so that at least a portion of the light being reflected by said reflecting means passes from said light source to said viewing point without passing through said light diffusing means.

2. An apparatus as defined in claim 1, wherein said light diffusing means comprises a translucent element.

3. An apparatus as defined in claim 2, wherein said light diffusing means is a glass plate.

4. An apparatus as defined in claim 1, wherein said light reflecting means comprises a wall portion of said envelope.

5. An apparatus as defined in claim 1, wherein said light reflecting means comprises a discrete structural element.

6. An apparatus as defined in claim 1, wherein said envelope comprises a light opaque structure.

7. An apparatus as defined in claim 1, further comprising an ultraviolet light source for illuminating said stone.

8. An apparatus as defined in claim 1, further comprising a light filter disposed between said light reflecting means.

9. An apparatus as defined in claim 1, wherein said light diffusing means comprises a translucent plate extending only to a point spaced apart from said light reflecting means.

10. An apparatus as defined in claim 1, wherein said light source is connected to a variable power source, so that the light intensity thereof can be varied.

11. An apparatus as defined in claim 1, wherein said light diffusing means serves as a support for said precious stone.

12. An apparatus as defined in claim 1 wherein said light source is an incandescent lamp.

* * * * *